United States Patent
Yacovan et al.

(10) Patent No.: US 10,633,352 B2
(45) Date of Patent: Apr. 28, 2020

(54) PROCESS FOR PREPARING 1,1,3-TRIOXO-1,2-BENZOTHIAZOLE-6-CARBOXAMIDE

(71) Applicants: Avihai Yacovan, Maxkeret Batya (IL); Yaniv Barda, Rehovot (IL); Sima Mirilashvili, Lod (IL); Shmuel A. Baron, Ashdod (IL)

(72) Inventors: Avihai Yacovan, Maxkeret Batya (IL); Yaniv Barda, Rehovot (IL); Sima Mirilashvili, Lod (IL); Shmuel A. Baron, Ashdod (IL)

(73) Assignee: ADAMA AGAN LTD., Ashdod (IL)

( * ) Notice: Subject to any disclaimer, the term of this patent is extended or adjusted under 35 U.S.C. 154(b) by 0 days.

(21) Appl. No.: 16/066,971

(22) PCT Filed: Dec. 28, 2016

(86) PCT No.: PCT/IB2016/001918
§ 371 (c)(1),
(2) Date: Jun. 28, 2018

(87) PCT Pub. No.: WO2017/115134
PCT Pub. Date: Jul. 6, 2017

(65) Prior Publication Data
US 2019/0002419 A1    Jan. 3, 2019

(30) Foreign Application Priority Data
Jan. 1, 2016    (IN) .............................. 201631000081

(51) Int. Cl.
*C07D 275/06*    (2006.01)

(52) U.S. Cl.
CPC .................................. *C07D 275/06* (2013.01)

(58) Field of Classification Search
None
See application file for complete search history.

(56) References Cited

U.S. PATENT DOCUMENTS 6,228,808 B1    5/2001   Kehne et al.

FOREIGN PATENT DOCUMENTS

CN    103 333 120 A    10/2013

OTHER PUBLICATIONS

Oscar Webber, "Ueber Sulfotoluyleaureimid (Methylseooharin)", Chemische Berichte, 25, 1892, Jan. 28, 2006.
International Search Report dated Mar. 16, 2017 in connection with PCT/IB2016/001918.
Written Opinion of the International Searching Authority dated Mar. 16, 2017 in connection with PCT/IB2016/001918.

*Primary Examiner* — Alicia L Otton
(74) *Attorney, Agent, or Firm* — Gary J. Gershik; Cooper & Dunham LLP

(57) ABSTRACT

A process for preparing, 1,1,3-Trioxo-1,2-benzothiazole-6-carboxamide of formula (I) comprising: reacting 2-chlorosulfonyl-terephthalic acid dialkyl ester of formula (II) with ammonia (N $H_3$) or ammonium containing-salt; wherein R represents a branched or non-branched $C_1$-$C_{12}$ alkyl.

21 Claims, No Drawings

PROCESS FOR PREPARING 1,1,3-TRIOXO-1,2-BENZOTHIAZOLE-6-CARBOXAMIDE

CROSS-REFERENCE TO RELATED APPLICATIONS

This application is a § 371 national stage of PCT International Application No. PCT/IB2016/001918, filed Dec. 28, 2016 and claims priority of Indian Provisional Application No. 201631000081, filed Jan. 1, 2016, the entire contents of each of which are hereby incorporated by reference.

TECHNICAL FIELD

The present subject matter relates to a process for preparing 1,1,3-Trioxo-1,2-benzothiazole-6-carboxamide.

BACKGROUND

The compound 1,1,3-Trioxo-1,2-benzothiazole-6-carboxamide of formula (I) is an important intermediate for preparing inter glia the herbicidal agents such as mesosulfuron-methyl.

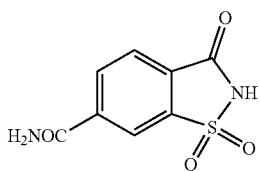
(I)

CN 103333120 describes a process for preparing mesosulfuron-methyl from p-toluic acid via the intermediate 1,2-benzisothiazole-6-carboxamide,2,3-dihydro-3-oxo-,1,1-dioxide. Chromates which are hazardous reagents are used in the oxidation step.

CN 104610167 describes a process for preparing mesosulfuron-methyl which includes the steps of reduction of 6-nitrosaccharin to obtain 6-amino saccharin under a condition that reduction catalyst exists and diazotization of the 6-amino saccharin to obtain 6-isonitrosomethyl.

CN 103755603 describes the preparation of Me 2-sulfamoyl-4-(methylsulfonamidomethyl)benzoate by the following steps: a reaction of p-(methylsulfonamidomethyl)toluene and chlorosulfonation agent (chlorosulfonic acid) at (−10)-0° C., and performing ammonolysis reaction in ammonia water at room temperature, to obtain 2-sulfa moyl-4-(methylsulfona midomethyptoluene; (2) oxidizing with potassium dichromate in concentrated sulfuric acid at (−4)-(−2)° C., to obtain 5-(methylsulfonamidomethyl)saccharin; and (3) dissolving in methanol, adding concentrated sulfuric acid, and performing alcoholysis reaction.

Based on the disadvantages in the above processes, it would be highly desirable to have an improved process for the production of the compound of formula (I) which is suitable for industrial use, highly efficient, low-cost, environmentally friendly, and provides a high yield in relatively short reaction time, thereby overcoming the deficiencies of the prior art. The present subject matter provides such a process.

It is therefore a purpose of the present subject matter to provide a process that overcomes the disadvantages of the known art.

SUMMARY

According to one aspect, the present subject matter provides a process for preparing 1,1,3-Trioxo-1,2-benzothiazole-6-carboxamide of formula (I) or a salt thereof

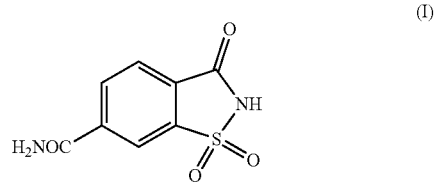 [SMILES: NC(=O)c1ccc2c(c1)S(=O)(=O)NC2=O]
(I)

by reacting 2-chlorosulfonyl-terephthalic acid dialkyl ester of formula (II)

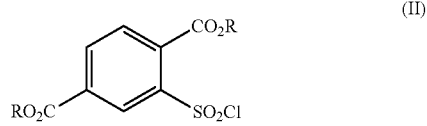
(II)

with ammonia ($NH_3$) or ammonium containing-salt, wherein R represents a branched or non-branched $C_1$-$C_{12}$ alkyl.

According to an embodiment, the ammonium containing-salt may selected from the group consisting of ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates and ammonium sulfide. The reaction may be performed in the presence of a solvent.

According to an embodiment, the molar ratio of the compound of formula (II) to the ammonia or ammonium-containing salt may be from 1:2 to 1:50. The reaction is carried at a temperature of from 0° C. to 150° C. The resulting compound of formula (I) may be present at a purity of at least 80%, at least 85%, at least 90%, at least 95%, at least 98%, or at least 99%.

According to a further embodiment, the compound of formula (II) may be prepared by the esterification of 2-sulfoterephthalic acid of formula (III) or a salt thereof;

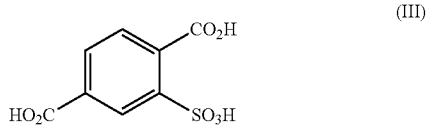
(III)

and subsequent chlorinating the resulting 2-sulfo-terephthalic acid dialkyl ester of formula (IV) or a salt thereof,

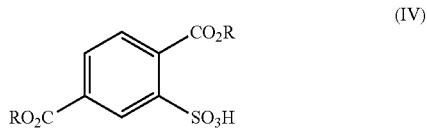
(IV)

wherein R represents a branched or non-branched $C_1$-$C_{12}$ alkyl.

According to an embodiment, the compound of formula (I), the compound of formula (III) and the compound of formula (IV) are in the form of a salt selected from the group consisting of ammonia salt, sodium salt, potassium salt, calcium salt and magnesium salt. The esterification may be carried out in the presence of (i) one of thionyl chloride, oxalyl chloride, phosgene, triphosgene, and (ii) an alcohol with the formula ROH, wherein R represents a branched or non-branched $C_1$-$C_{12}$ alkyl. In another embodiment, the esterification may be carried out in the presence of an acid selected from the group consisting of sulfuric acid, hydrochloric acid, nitric acid, hydroiodic acid and p-toluene sulfonic acid, and an alcohol with the formula ROH, wherein R represents a branched or non-branched $C_1$-$C_{12}$ alkyl.

The chlorination is carried out in the presence of a chlorinating agent and at least one polar aprotic solvent. In another embodiment, the chlorination is carried out in the presence of a chlorinating agent, a polar aprotic solvent and a non-polar solvent. The chlorinating agent may be selected from the group consisting of phosphorus oxychloride, thionyl chloride, phosgene, sulfuryl chloride, phosphorus pentachloride, triphosgene, diphosgene, and chlorine, oxalyl chloride. The polar aprotic solvent may be selected from the group consisting of, acetonitrile, methyl tert-butyl ether, tetrahydrofuran, dichloromethane, 1,2 dichloroethane, dimethylformamide, dimethylacetamide, ethyl acetate, acetone, dimethyl sulfoxide methyl iso-butyl ketone, isopropylacetate 2-Methyltetrahydrofuran, 1,4-dioxane, CPME, dimethoxyethane, diglyme and diethoxymethane and the non-polar solvent may be selected from the group consisting of n-Heptane, n-Octane, cyclohexane, methyl-cyclohexane, benzene, toluene, xylene, cumene, tetraline, and anisole.

According to a further aspect, the present subject matter provides a process for preparing 1,1,3-Trioxo-1,2-benzothiazole-6-carboxamide of formula (I) or a salt thereof

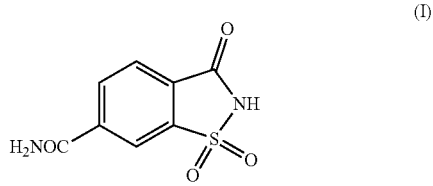 [SMILES: NC(=O)c1ccc2c(c1)S(=O)(=O)NC2=O]

(I)

by esterifying 2-sulfo-terephthalic acid of formula (III) or a salt thereof;

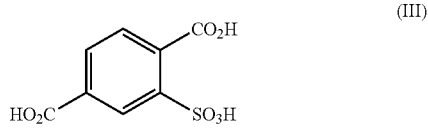

(III)

chlorinating the resulting 2-sulfo-terephthalic acid dialkyl ester of formula (IV) or a salt thereof; and

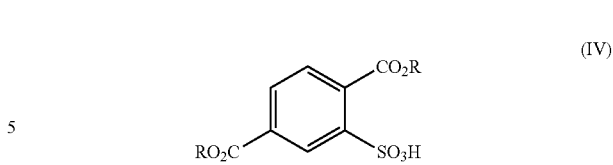

(IV)

reacting the formed 2-chlorosulfonyl-terephthalic acid dialkyl ester of formula (II)

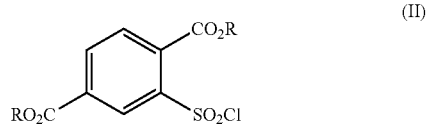

(II)

with ammonia ($NH_3$) or an ammonium-containing salt, wherein R represents a branched or non-branched $C_1$-$C_{12}$ alkyl.

According to an embodiment, the ammonium containing-salt may be selected from the group consisting of ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates and ammonium sulfide. The compound of formula (I), the compound of formula (III) and the compound of formula (IV) are in the form of a salt selected from the group consisting of ammonia salt, sodium salt, potassium salt, calcium salt and magnesium salt. The reaction may be performed in the presence of a solvent.

According to an embodiment, the molar ratio of the compound of formula (II) to the ammonia or ammonium-containing salt may be from 1:2 to 1:50. The reaction is carried at a temperature of from 0° C. to 150° C. The resulting compound of formula (I) may be present at a purity of at least 80%, at least 85%, at least 90%, at least 95%, at least 98%, or at least 99%.

According to an embodiment, the compound of formula (I), the compound of formula (III) and the compound of formula (IV) are in the form of a salt selected from the group consisting of ammonia, salt, sodium salt, potassium salt, calcium salt and magnesium salt. The esterification may be carried out in the presence of (i) one of thionyl chloride, oxalyl chloride, phosgene, triphosgene, and (ii) an alcohol with the formula ROH, wherein R represents a branched or non-branched $C_1$-$C_{12}$ alkyl. In another embodiment, the esterification may be carried out in the presence of an acid selected from the group consisting of sulfuric acid, hydrochloric acid, nitric acid, hydroiodic acid and p-toluene sulfonic acid, and an alcohol with the formula ROH, wherein R represents a branched or non-branched $C_1$-$C_{12}$ alkyl.

The chlorination is carried out in the presence of a chlorinating agent and at least one polar aprotic solvent. In another embodiment, the chlorination is carried out in the presence of a chlorinating agent, a polar aprotic solvent and a non-polar solvent. The chlorinating agent may be selected from the group consisting of phosphorus oxychloride, thionyl chloride, phosgene, sulfuryl chloride, phosphorus pentachloride, triphosgene, diphosgene, and chlorine, oxalyl chloride. The polar aprotic solvent may be selected from the group consisting of, acetonitrile, methyl tert-butyl ether, tetrahydrofuran, dichloromethane, 1,2 dichloroethane, dimethylformamide, dimethylacetamide, ethyl acetate, acetone, dimethyl sulfoxide methyl iso-butyl ketone, isopropylacetate 2-Methyltetrahydrofuran, 1,4-dioxane, CPME, dimethoxyethane, diglyme and diethoxymethane, and the nonpolar solvent may be selected from the group consisting of n-Heptane, n-Octane, cyclohexane, methyl-cyclohexane, benzene, toluene, xylene, cumene, tetraline, and anisole.

According to a further aspect, the present subject matter provides a process for preparing 1,1,3-Trioxo-1,2-benzothiazole-6-carboxamide of formula (I) or a salt thereof

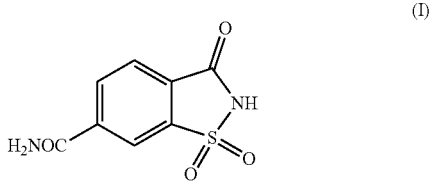
(I)

by chlorinating 2-sulfo-terephthalic acid dialkyl ester of formula (IV) or a salt thereof; and

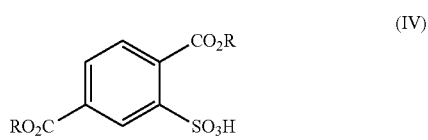
(IV)

reacting the formed 2-chlorosulfonyl-terephthalic acid dialkyl ester of formula (II)

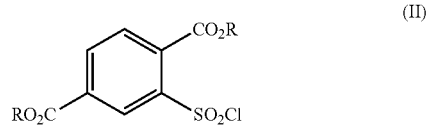
(II)

with ammonia ($NH_3$) or an ammonium-containing salt; wherein the compound of formula (II) is not isolated prior to its reaction with the ammonia or ammonium-containing salt; and wherein R represents a branched or non-branched $C_1$-$C_{12}$ alkyl.

According to an embodiment, the ammonium containing-salt may be selected from the group consisting of ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates and ammonium sulfide. The compound of formula (I), the compound of formula (III) and the compound of formula (IV) are in the form of a salt selected from the group consisting of ammonia salt, sodium salt, potassium salt, calcium salt and magnesium salt. The reaction may be performed in the presence of a solvent. The reaction may be carried out in the presence of phosphorus oxychloride, thionyl chloride, phosgene, sulfuryl chloride, phosphorus pentachloride, triphosgene, diphosgene, and chlorine, oxalyl chloride.

According to an embodiment, the molar ratio of the compound of formula (II) to the ammonia or ammonium-containing salt may be from 1:2 to 1:50. The reaction is carried at a temperature of from 0° C. to 150° C. The resulting compound of formula (I) may be present at a purity of at least 80%, at least 85%, at least 90%, at least 95%, at least 98%, or at least 99%.

In an embodiment, the herein described processes may be used in the production of mesosulfuron-methyl.

In another embodiment, the present subject matter relates to the use of the compound of formula (I) as prepared according to processes disclosed herein in the preparation of mesosulfuron-methyl.

DETAILED DESCRIPTION

Definitions

Prior to setting forth the present subject matter in detail, it may be helpful to provide definitions of certain terms to be used herein. Unless defined otherwise, all technical and scientific terms used herein have the same meaning as is commonly understood by one of skill in the art to which this subject matter pertains.

The term "a" or "an" as used herein includes the singular and the plural, unless specifically stated otherwise. Therefore, the terms "a," "an," or "at least one" can be used interchangeably in this application.

Throughout the application, descriptions of various embodiments use the term "comprising"; however, it will be understood by one of skill in the art, that in some specific instances, an embodiment can alternatively be described using the language "consisting of essentially of" or "consisting of".

For purposes of better understanding the present teachings and in no way limiting the scope of the teachings, unless otherwise indicated, all numbers expressing quantities, percentages, or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. In this regard, used of the term "about" herein specifically includes ±10% from the indicated values in the range. In addition, the endpoints of all ranges directed to the same component or property herein are inclusive of the endpoints, are independently combinable, and include all intermediate points and ranges.

Process for Preparing
1,1,3-Trioxo-1,2-benzothiazole-6-carboxamide

The present subject matter provides an process for preparing 1,1,3-Trioxo-1,2-benzothiazole-6-carboxamide of formula (I) or a salt thereof

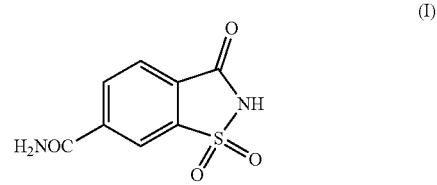 [SMILES: NC(=O)c1ccc2c(c1)S(=O)(=O)NC2=O]
(I)

wherein the process comprises reacting 2-chlorosulfonyl-terephthalic acid dialkyl ester of formula (II)

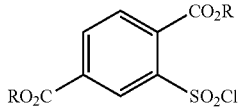
(II)

with ammonia (NH$_3$) or ammonium containing-salt. R may be defined as a branched or non-branched $C_1$-$C_{12}$ alkyl. In a preferred embodiment, R may be defined as methyl or ethyl.

In another embodiment, the present subject matter provides a process for preparing 1,1,3-Trioxo-1,2-benzothiazole-6-carboxamide of formula (I) or a salt thereof

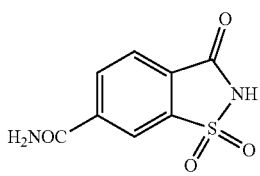
(I)

wherein the process comprises esterifying 2-sulfo-terephthalic acid of formula (III) or a salt thereof;

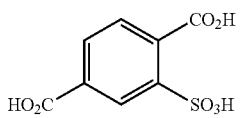
(III)

chlorinating the resulting 2-sulfo-terephthalic acid dialkyl ester of formula (IV) or a salt thereof; and

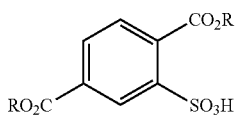
(IV)

reacting the formed 2-chlorosulfonyl-terephthalic acid dialkyl ester of formula (II)

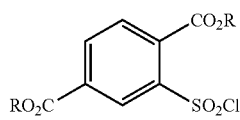
(II)

with ammonia (NH$_3$) or an ammonium-containing salt. R may be defined as a branched or non-branched $C_1$-$C_{12}$ alkyl. In a preferred embodiment, R may be defined as methyl or ethyl.

The present process is advantageous in that the process is highly efficient, providing a short reaction time.

The resulting compound of formula (II) is subsequently reacted with ammonia (NH$_3$) or ammonium containing-salt to form the compound of formula (I). According to an embodiment, the compound of formula (II) may be isolated prior to its reaction with the ammonia or ammonium-containing salt. According to another embodiment, the compound of formula (II) is not isolated prior to its reaction with the ammonia or ammonium-containing salt.

In an embodiment of the present process, the ammonium containing-salt is selected from the group consisting of ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates and ammonium sulfide. In a specific example, 2-chlorosulfonyl-terephthalic acid dialkyl ester of formula (II) is reacted with ammonium hydroxide to form 1,1,3-Trioxo-1,2-benzothiazole-6-carboxamide of formula (I).

In one embodiment, the reaction to form the compound of formula (I) from the compound of formula (II) is carried out in the presence of a solvent. The solvent may be selected from the group consisting of alcohols such as methanol, ethanol, isopropanol, tert-butanol; chlorinated and brominated solvents such as dichloromethane, 1, 2-dichloroethane, 1,2-dibromoethane, chlorobenzene; aromatic solvents such as toluene and xylene; N-Methyl-2-pyrrolidone, tetrahydrofuran, methyl tert-butyl ether, 1,4-dioxane, dimethoxyethane, diethoxymethane, methyltetrahydrofuran, CPME, acetonitrile and water.

The present process is advantageous in that it avoids the need for using hazardous reagents such as chromates and permanganates. The present process furthermore provides a shorter reaction time. In addition, the process is highly efficient providing higher yields and purities of 1,1,3-Trioxo-1,2-benzothiazole-6-carboxamide thus leading to higher yields and purities of the final product.

In an embodiment of the present processes, the molar ratio between the compound of formula (II) and the ammonia or ammonium-containing salt is from about 1:2 to about 1:100. In another embodiment, the molar ratio between the compound of formula (II) and the ammonia or ammonium-containing salt is from about 1:2 to about 1:50. In yet another embodiment, the molar ratio between the compound of formula (II) and the ammonia or ammonium-containing salt is from about 1:2 to about 1:30. In a further embodiment, the molar ratio between the compound of formula (II) and the ammonia or ammonium-containing salt is from about 1:2 to about 1:20. In a specific embodiment, the molar ratio between the compound of formula (II) and the ammonia or ammonium-containing salt is about 1:13.

In one embodiment, the reaction to form the compound of formula (I) from the compound of formula (II) is conducted at a temperature from about 20° C. to about 100° C., preferably from about 25° C. to about 80° C., more preferably from about 50° C. to about 70° C. In a preferred embodiment, the reaction is conducted at a temperature from about 55° C. to about 65° C. In another embodiment, the reaction to form the compound of formula (I) from the compound of formula (II) is conducted at a temperature from about 20° C. to about 100° C., preferably from about 30° C. to about 90° C., more preferably from about 55° C. to about 85° C. In a preferred embodiment, the reaction is conducted at a temperature from about 80° C. to about 85° C.

In one embodiment, the process for preparing 1,1,3-Trioxo-1,2-benzothiazole-6-carboxamide may conducted at a pressure from about 1 bar to about 100 bar. In another embodiment, the process may be conducted at a pressure from about 1 bar to about 50 bar. In yet another embodiment, the process may be conducted at a pressure from about 1 bar to about 15 bar. In a preferred embodiment, the process for preparing 1,1,3-Trioxo-1,2-benzothiazole-6-carboxamide may conducted at atmospheric pressure. In another preferred embodiment, the process may be conducted at about 50 bar. In certain embodiments, it may be preferred that the process is conducted at pressures less than atmospheric pressure. For example, the process may be carried out at 0.7 bar, 0.75 bar, 0.8 bar, 0.9 bar or 0.95 bar.

According to an embodiment, the compound of formula (I) is present at a purity of at least 80%, at least 85%, at least 88%, at least 89%, at least 90%, at least 91%, at least 92%, at least 93%, at least 94%, at least 95%, at least 96%, at least 97%, at least 98%, or at least 99%.

In another embodiment the present subject matter provides a process for preparing 2-chlorosulfonyl-terephthalic acid dialkyl ester of formula (II) wherein the process comprises the esterification of 2-sulfo-terephthalic acid of formula (III) or a salt thereof

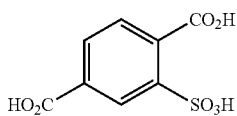

(III)

and subsequent chlorination of the resulting 2-sulfo-terephthalic acid dialkyl ester of formula (IV) or a salt thereof;

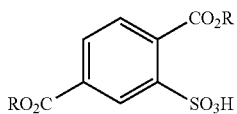

(IV)

wherein R represents a branched or non-branched $C_1$-$C_{12}$ alkyl. In a preferred embodiment, R may be defined as methyl or ethyl.

In an embodiment of the present process the compound of formula (I), the compound of formula (III) and the compound of formula (IV) are in the form of a salt. Examples of salts may include but are not limited to ammonia salt, sodium salt, potassium salt, calcium salt and magnesium salt.

According to an embodiment, the esterification may be carried out in the presence of (i) one of thionyl chloride, oxalyl chloride, phosgene, triphosgene, and (ii) an alcohol with the formula ROH, wherein R represents a branched or non-branched $C_1$-$C_{12}$ alkyl. In another embodiment, the esterification may be carried out in the presence of an acid selected from the group consisting of sulfuric acid, hydrochloric acid, nitric acid, hydroiodic acid and p-toluene sulfonic acid, and an alcohol with the formula ROH, wherein R represents a branched or non-branched $C_1$-$C_{12}$ alkyl. In a preferred embodiment, the esterification is performed in methanol or ethanol in the presence of sulfuric acid.

According to an embodiment, the chlorination is carried out in the presence of a chlorinating agent and at least one polar aprotic solvent. The chlorinating agent may be selected from the group consisting of phosphorus oxychloride, thionyl chloride, phosgene, sulfuryl chloride, phosphorus pentachloride, triphosgene, diphosgene, and chlorine, oxalyl chloride. The polar aprotic solvent may be selected from the group consisting of, acetonitrile, methyl tert-butyl ether, tetrahydrofuran, dichloromethane, 1,2 dichloroethane, dimethylformamide, dimethylacetamide, ethyl acetate, acetone, dimethyl sulfoxide methyl iso-butyl ketone, isopropylacetate 2-Methyltetrahydrofuran, 1,4-dioxane, CPME, dimethoxyethane, diglyme and diethoxymethane. In a preferred embodiment, the chlorination is carried out in the presence of phosphorus oxychloride and acetonitrile.

According to an embodiment, the chlorination is carried out in the presence of a chlorinating agent selected from the group disclosed hereinabove, a polar aprotic solvent and a non-polar solvent. The polar aprotic solvent may be selected from the group disclosed hereinabove. The non-polar solvent may be selected from the group consisting of hydrocarbons such as: n-Heptane, n-Octane, cyclohexane, methylcyclohexane, benzene, toluene, xylene, cumene, tetraline; and ethers such as: anisole. In a preferred embodiment, the chlorination is carried out in the presence of phosphorus oxychloride, acetonitrile, and toluene.

One-Pot Process for Preparing 1,1,3-Trioxo-1,2-benzothiazole-6-carboxamide

In another embodiment the present subject matter provides a process for preparing 1,1,3-Trioxo-1,2-benzothiazole-6-carboxamide of formula (I) or a salt thereof

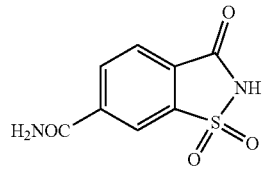

(I)

wherein the process comprises chlorinating 2-sulfo-terephthalic acid dialkyl ester of formula (IV) or a salt thereof; and

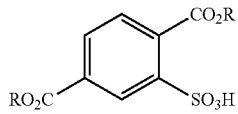

(IV)

reacting the formed 2-chlorosulfonyl-terephthalic acid dialkyl ester of formula (II)

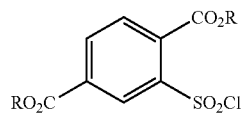

(II)

with ammonia ($NH_3$) or an ammonium-containing salt. According to an embodiment, the compound of formula (II) is not isolated prior to its reaction with the ammonia or ammonium-containing salt. R may be defined as a branched or non-branched $C_1$-$C_{12}$ alkyl. In a preferred embodiment, R may be defined as methyl or ethyl.

In an embodiment of the present process, the ammonium containing-salt is selected from the group consisting of ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates and ammonium sulfide. In a specific example, 2-chlorosulfonyl-terephthalic acid dialkyl ester of formula (II) is reacted with ammonium hydroxide to form 1,1,3-Trioxo-1,2-benzothiazole-6-carboxamide of formula (I).

In an embodiment of the present process, the compound of formula (I) and the compound of formula (IV) are in the form of a salt. Examples of salts may include but are not limited to ammonia salt, sodium salt, potassium salt, calcium salt and magnesium salt.

In one embodiment, the reaction to form the compound of formula (I) from the compound of formula (II) is carried out in the presence of a solvent. The solvent may be selected from the group consisting of alcohols such as methanol, ethanol, isopropanol, tert-butanol; chlorinated and brominated solvents such as dichloromethane, 1,2-dichloroethane, 1,2-dibromoethane, chlorobenzene; hydrocarbons such as: n-Heptane, n-Octane, cyclohexane, methyl-cyclohexane; aromatic solvents such as benzene, toluene and xylene; N-Methyl-2-pyrrolidone, tetrahydrofuran, methyl tert-butyl ether, 1,4-dioxane, dimethoxyethane, diethoxymethane, methyltetrahydrofuran, CPME, acetonitrile and water.

According to an embodiment, the chlorination is carried out in the presence of a chlorinating agent selected from the group consisting of phosphorus oxychloride, thionyl chloride, phosgene, sulfuryl chloride, phosphorus pentachloride, triphosgene, diphosgene, and chlorine, oxalyl chloride.

The present one-pot process reduces the cost of production, simplifies work-up, and minimizes any effluent disposal problems.

According to an embodiment, the resultant product comprises compound of formula (I) with a purity of at least 80%, at least 85%, at least 88%, at least 89%, at least 90%, at least 91%, at least 92%, at least 93%, at least 94%, at least 95%, at least 96%, at least 97%, at least 98%, or at least 99%.

The compound of formula (I) is an important intermediate and may be used in the preparation of mesosulfuron-methyl, as described in CN 103333120, incorporated herein by reference in its entirety.

In a further aspect of the subject matter there is provided a process for preparation of mesosulfuron-methyl comprising:
a) preparing compound of formula (I) as described herein;
b) providing reaction conditions for preparation of mesosulfuron-methyl.

According to an embodiment the reaction conditions in step (b) include but are not limited to oxidation, reduction, ring opening, sulfonylation and coupling to obtain mesosulfuron-methyl.

The progress of the reaction can be monitored using any suitable method, which can include, for example, chromatographic methods such as, e.g., high performance liquid chromatography (HPLC), thin layer chromatography (TLC), and the like.

In yet another embodiment, the compound of formula (I) can be isolated from the reaction mixture by any conventional techniques well-known in the art. Such isolation techniques can be selected, without limitation, from the group consisting of concentration, extraction, precipitation, cooling, filtration, crystallization, centrifugation, and a combination thereof, followed by drying.

In yet another embodiment, the compound of formula (I) can be optionally purified by any conventional techniques well-known in the art. Such purification techniques can be selected, without limitation, from the group consisting of precipitation, crystallization, extraction, slurrying, washing in a suitable solvent, filtration through a packed-bed column, dissolution in an appropriate solvent, re-precipitation by addition of a second solvent in which the compound is insoluble, and a combination thereof.

The following examples illustrate the practice of the present subject matter in some of its embodiments, but should not be construed as limiting the scope of the present subject matter. Other embodiments will be apparent to one skilled in the art from consideration of the specification and examples. It is intended that the specification, including the examples, is considered exemplary only without limiting the scope and spirit of the present subject matter.

Example 1

An exemplary experimental procedure for producing, 1,3-Trioxo-1,2-benzothiazole-6-carboxamide of formula (I) is described as follows:

Step 1: Preparation of 2-Sulfo-Terephthalic Acid (Compound (III))

10 g (60 mmol) of terephthalic acid and 0.1 g of iron(II) sulfate heptahydrate were placed in flask. 10 ml of oleum (65% of $SO_3$) was then added to the flask. Reaction mixture was heated to a temperature of 210° C. for 16 hours. The mixture was then cooled to 50° C. and poured onto ice (200 ml). 5 g of NaCl were added and the clear solution was kept at 5° C. for 18 hours. Resulted crystals were collected by filtration and dried in a vacuum.
Yield: 12 g (75%). Additional amount of product could be obtained after concentration of filtrate.

Step 2: Preparation of 2-Sulfo-Terephthalic Acid Dimethyl Ester (Compound (IV))

A solution of 1.00 g (4.06 mmol) of 2-sulfo-terephthalic acid (Compound III) and 2 drops (~5 mol %) of sulfuric acid in 20 ml of methanol was heated under reflux to 65° C. for 16 hours. The methanol was evaporated and the resulting solid was crystallized from water after the addition of NaCl.
Yield: 0.72 g (65%).

Step 3: Preparation of 2-Chlorosulfonyl-Terephthalic Acid Dimethyl Ester (Compound (II))

89.3 g, (325.6 mmol, 1.0 eq.) of 2-Sulfo-terephthalic acid dimethyl ester (Compound (IV)) was suspended in 250 ml dry acetonitrile and $POCl_3$ (62 mL, 651 mmol, 2.0 eq.) was added dropwise, over 1 hour, to the reaction flask. When the addition was completed the reaction mixture was heated to 80-90° C. and stirred until the starting material was fully consumed. During the stirring, the color of the suspension turned yellow. Reaction progress was monitored by HPLC. When the heating was stopped, the mixture was carefully poured onto ice water (200 g). Ethyl acetate (400 ml) was added and the layers were separated. The organic phase was washed with water (200 ml), dried over $Na_2SO_4$, filtrated and evaporated under reduced pressure. The desired product was obtained as yellowish oil: Yield: 81.8 g (87%), Purity: 90%.

Step 4: Preparation of 1,1,3-Trioxo-1,2-benzothiazole-6-carboxamide (Compound (I))

A solution of 20 g, (68.3 mmol, 1 eq.) 2-Chlorosulfonyl-terephthalic acid dimethyl ester (Compound (II)) in dry acetonitrile (15 ml) was placed in a pressure tube and cooled in an ice-water bath. A solution of 28% ammonia (ammonium hydroxide) (60 ml, 10 eq.) was added dropwise over 20 minutes. A white solid was formed immediately. The mixture was heated to 60° C. and stirred until the starting material was fully consumed (3 hours). The heating was stopped and the mixture was cooled to room temperature. The resulting precipitate was filtered off and washed with water (10 ml). Drying in high vacuum afforded the pure desired product as an off-white solid.

Purity of 1,1,3-Trioxo-1,2-benzothiazole-6-carboxamide: 93%.

Yield of 1,1,3-Trioxo-1,2-benzothiazole-6-carboxamide: 13.1 g (84.8%).

Example 2

An exemplary experimental procedure for producing 1,1,3-Trioxo-1,2-benzothiazole-6-carboxamide of formula (I) is described as follows:

Preparation of 1,1,3-Trioxo-1,2-benzothiazole-6-carboxamide (Compound (I))

In this example, 2-Sulfo-terephthalic acid dimethyl ester (Compound IV) may be prepared in accordance with Steps 1-2 of Example 1.

200 g (0.73 mol) of 2-Sulfo-terephthalic acid dimethyl ester (Compound IV) was suspended in 300 ml of dry acetonitrile and the reaction mixture was heated to 75° C. $POCl_3$ (116.4 g, 71 ml, 0.76 mol) was added dropwise, over 20 minutes, to the reaction mixture. When the addition was completed the reaction mixture was stirred at 80° C. until the starting material was fully consumed. The reaction mixture was cooled to 25° C. and added in portions to a cooled solution (0° C.) of 25% ammonium hydroxide (600 ml, 10 eq.), while keeping the reaction temperature below 25° C. The reaction mixture was stirred at room temperature overnight and the reaction progress was monitored by HPLC. The suspension was filtered and the filtrate was dried in vacuum to obtain 1,1,3-Trioxo-1,2-benzothiazole-6-carboxamide of formula (I).

Yield of 1,1,3-Trioxo-1,2-benzothiazole-6-carboxamide: 158 g (95%).

As demonstrated in the above example, a high yield of 1,1,3-Trioxo-1,2-benzothiazole-6-carboxamide may be produced using the process described hereinabove. The results demonstrate a high level efficiency of the reaction.

While the present subject matter has been shown and described with reference to preferred embodiments thereof, it will be understood by those skilled in the art that many alternatives, modifications and variations may be made thereto without departing from the spirit and scope thereof. Accordingly, it is intended to embrace all such alternatives, modifications, and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:

1. A process for preparing 1,1,3-Trioxo-1,2-benzothiazole-6-carboxamide of formula (I) or a salt thereof

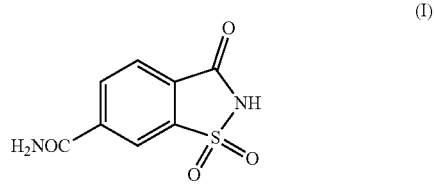 [SMILES: NC(=O)c1ccc2c(c1)S(=O)(=O)NC2=O]

the process comprising:
reacting 2-chlorosulfonyl-terephthalic acid dialkyl ester of formula (II)

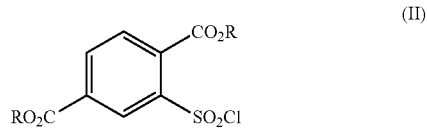

with ammonia (NH3) or ammonium containing-salt;
wherein R represents a branched or non-branched $C_1$-$C_{12}$ alkyl.

2. The process of claim 1, wherein the ammonium containing-salt is selected from the group consisting of ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates and ammonium sulfide.

3. The process of claim 1, wherein the reaction is performed in the presence of a solvent.

4. The process of claim 1, wherein the molar ratio of the compound of formula (II) to the ammonia or ammonium-containing salt is from 1:2 to 1:50.

5. The process of claim 1, wherein the reaction is carried at a temperature of from 0° C. to 150° C.

6. The process of claim 1, wherein the resulting compound of formula (I) is present at a purity of at least 80%, at least 85%, at least 90%, at least 95%, at least 98%, or at least 99%.

7. The process of claim 1, wherein the compound of formula (II) is prepared by the esterification of 2-sulfo-terephthalic acid of formula (III) or a salt thereof;

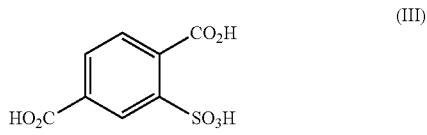

and subsequent chlorination of the resulting 2-sulfo-terephthalic acid dialkyl ester of formula (IV); or a salt thereof

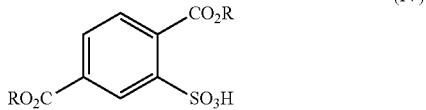

(IV)

wherein R is branched or non-branched $C_1$-$C_{12}$ alkyl.

8. The process of claim 7, wherein the compound of formula (I), the compound of formula (III) and the compound of formula (IV) are in the form of a salt, wherein the salt is selected from the group consisting of ammonia salt, sodium salt, potassium salt, calcium salt and magnesium salt.

9. The process of claim 7, wherein the esterification is carried out in the presence of (i) one of thionyl chloride, oxalyl chloride, phosgene, triphosgene, or an acid selected from the group consisting of sulfuric acid, hydrochloric acid, nitric acid, hydroiodic acid and p-toluene sulfonic acid and (ii) an alcohol with the formula ROH, wherein R represents a branched or non-branched $C_1$-$C_{12}$ alkyl.

10. The process of claim 9, wherein the chlorinating agent is selected from the group consisting of phosphorus oxychloride, thionyl chloride, phosgene, sulfuryl chloride, phosphorus pentachloride, triphosgene, diphosgene, chlorine, and oxalyl chloride, wherein the polar aprotic solvent is selected from the group consisting of acetonitrile, methyl tert-butyl ether, tetrahydrofuran, dichloromethane, 1,2 dichloroethane, dimethylformamide, dimethylacetamide, ethyl acetate, acetone, dimethyl sulfoxide methyl iso-butyl ketone, isopropylacetate 2-Methyltetrahydrofuran, 1,4-dioxane, CPME, dimethoxyethane, diglyme and diethoxymethane and the non-polar solvent is selected from the group consisting of n-Heptane, n-Octane, cyclohexane, methylcyclohexane, benzene, toluene, xylene, cumene, tetraline, and anisole.

11. The process of claim 7, wherein the chlorination is carried out' in the presence of a chlorinating agent and at least one polar aprotic solvent, and optionally a non-polar solvent.

12. The process of claim 11, wherein the ammonium containing-salt is selected from the group consisting of ammonium hydroxide, ammonium chloride, ammonium bromide, ammonium sulfate, ammonium acetate, ammonium chlorate, ammonium carbonates, ammonium fluoride, ammonium bicarbonate, ammonium iodide, ammonium sodium hydrogen phosphate, ammonium nitrite, ammonium nitrate, ammonium phosphates and ammonium sulfide.

13. The process of claim 11, wherein the compound of formula (I) and the compound of formula (IV) are in the form of a salt, wherein the salt is selected from the group consisting of ammonia salt, sodium salt, potassium salt, calcium salt and magnesium salt.

14. The process of claim 11, wherein the reaction is performed in the presence of a solvent.

15. The process of claim 11, wherein the reaction is carried out in the presence of phosphorus oxychloride, thionyl chloride, phosgene, sulfuryl chloride, phosphorus pentachloride, triphosgene, diphosgene, and chlorine, oxalyl chloride.

16. The process of claim 11, wherein the molar ratio of the compound of formula (II) to the ammonia (NH3) or ammonium-containing salt is from 1:2 to 1:50.

17. The process of claim 11, wherein the reaction is carried at a temperature of from 0° C. to 150° C.

18. The process of claim 11, wherein the resulting compound of formula (I) is present at a purity of at least 80%, at least 85%, at least 90%, at least 95%, at least 98%, or at least 99%.

19. A process for preparing 1,1,3-Trioxo-1,2-benzothiazole-6-carboxamide of formula (I) or a salt thereof

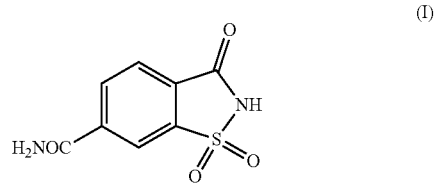 [SMILES: NC(=O)c1ccc2c(c1)S(=O)(=O)NC2=O]

(I)

the process comprising:
chlorinating 2-sulfo-terephthalic acid dialkyl ester of formula (IV) or a salt thereof; and

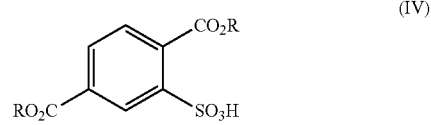

(IV)

reacting the formed 2-chlorosulfonyl-terephthalic acid dialkyl ester of formula (II)

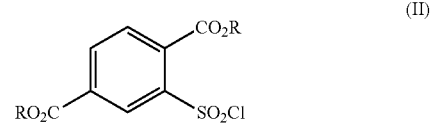

(II)

with ammonia (NH3) or an ammonium-containing salt;
wherein the compound of formula (II) is not isolated prior to its reaction with the ammonia or ammonium-containing salt; and
wherein R represents a branched or non-branched $C_1$-$C_{12}$ alkyl.

20. In a process for preparing mesosulfuron-methyl, the improvement comprising reacting an intermediate of formula (I) prepared according to claim 1.

21. In a process for preparing mesosulfuron-methyl, the improvement comprising reacting an intermediate of formula (I) prepared according to claim 19.

* * * * *